(12) United States Patent
Lee

(10) Patent No.: US 7,803,133 B2
(45) Date of Patent: Sep. 28, 2010

(54) FLOW CONTROLLERS

(76) Inventor: Freddie Eng Hwee Lee, No 6 Battery Road # 17-03, Singapore (SG) 049909

( * ) Notice: Subject to any disclaimer, the term of this patent is extended or adjusted under 35 U.S.C. 154(b) by 482 days.

(21) Appl. No.: 11/626,129

(22) Filed: Jan. 23, 2007

(65) Prior Publication Data
US 2008/0177233 A1   Jul. 24, 2008

(51) Int. Cl.
*A61M 1/00* (2006.01)
(52) U.S. Cl. .................................... 604/151
(58) Field of Classification Search ............ 604/151
See application file for complete search history.

(56) References Cited

U.S. PATENT DOCUMENTS

| 3,618,637 | A |   | 11/1971 | Santomieri |
| 4,397,335 | A |   | 8/1983 | Doblar |
| 4,802,650 | A | * | 2/1989 | Stricker ............... 251/117 |
| 2004/0173167 | A1 |   | 9/2004 | Chanfreau |
| 2005/0277884 | A1 |   | 12/2005 | Kriesel |
| 2007/0006621 | A1 | * | 1/2007 | Doong .................. 70/409 |
| 2008/0017260 | A1 | * | 1/2008 | Oh et al. ............... 137/625.3 |

FOREIGN PATENT DOCUMENTS

| DE | 43 23 613 | 1/1995 |
| EP | 0 800 837 | 10/1997 |
| WO | 2008/011246 | 1/2008 |

OTHER PUBLICATIONS

International Preliminary Report on Patentability, The International Bureau of WIPO, Aug. 6, 2009.

* cited by examiner

*Primary Examiner*—Nicholas D Lucchesi
*Assistant Examiner*—Jason Flick
(74) *Attorney, Agent, or Firm*—Occhiuti Rohlicek & Tsao LLP

(57) ABSTRACT

An apparatus for selecting a flow rate of a fluid includes an axle including an elongated cylindrical member having flow paths, each flow path being defined by a corresponding set of radial holes, each set of radial holes comprising at least one radial hole that extends substantially between an outer surface of the axle and an interior cavity of the axle, and a barrel including an elongated cylindrical member within which the axle is disposed, the barrel having input ports and an output port, the barrel being configured to enable the axle to rotate about an axis of rotation that extends along a length of the axle, wherein a flow rate of a fluid is selected by rotating the axle to a position so that a set of radial holes is in alignment with one or more ports of the barrel.

34 Claims, 4 Drawing Sheets

100

FLOW CONTROLLERS

BACKGROUND

This description relates to flow controllers.

A flow controller regulates the flow rate of a fluid from a source, e.g., a fluid pump, to a final receiving point, e.g., a patient, through one or more fluid-carrying channels, e.g., silicone-based tubes. In the context of a patient receiving medication, a flow controller allows for adjustment of the dose of medication as deemed appropriate during therapy. Flow controllers have been used in conjunction with fluid pumps that have fixed rates of flow output.

Typically, flow controllers operate on the concept that flow rates of a fluid through a fluid-carrying channel vary according to the diameter of a lumen of the channel, or according to a length of the channel, if other factors such as temperature and viscosity remain constant. This is based on Bernoulli's Principle. Conventional flow controllers achieve different flow rates by pinching off (e.g., clamping, pressing or occluding) one or more fluid-carrying channels using a teeth/groove or plunger (spring and non-spring loaded) mechanism, or by selectively opening and closing one or more fluid-carrying channels using a cam mechanism. Over time, such mechanical mechanisms have led to reduced structural integrity of the fluid-carrying channels even though pliable materials such as silicone tubes are used to reduce memory related issues. Such mechanical mechanisms have also employed leak-prone complex couplings to connect the desired fluid-carrying channel(s) to a distal end of the flow. In addition, flow controllers have not been easily portable due to complexity and size.

SUMMARY

In general, in one aspect, an apparatus for selecting a flow rate of a fluid includes an axle including an elongated cylindrical member having flow paths, each flow path being defined by a corresponding set of radial holes, each set of radial holes comprising at least one radial hole that extends substantially between an outer surface of the axle and an interior cavity of the axle, and a barrel including an elongated cylindrical member within which the axle is disposed, the barrel having input ports and an output port, the barrel being configured to enable the axle to rotate about an axis of rotation that extends along a length of the axle, wherein a flow rate of a fluid is selected by rotating the axle to a position so that a set of radial holes is in alignment with one or more ports of the barrel.

Implementations may include one or more of the following features. The apparatus further includes a holding reservoir including an input port and output ports, the input port for introducing the fluid into the holding reservoir, each output port for dispensing fluid from the holding reservoir. The holding reservoir is in fluid communication with a source of the fluid through a delivery line coupled to the input port of the holding reservoir. The source of the fluid includes a fluid pump. The apparatus further includes fluid-carrying channels, each fluid-carrying channel being coupled to a respective one of the output port of the holding reservoir. The interior cavity of the axle is in fluid communication with a destination of the fluid through a delivery line coupled to the output port of the barrel when a rotation of the axle results in a radial hole of the axle being in alignment with the output port of the barrel. The destination of the fluid includes a patient. The apparatus further includes N fluid-carrying channels, where N is an integer greater than or equal to two, each fluid-carrying channel being coupled to a respective one of the input ports of the barrel. Each fluid-carrying channel includes a micro bore tube that controls a rate at which fluid passes through the fluid-carrying channel. The fluid-carrying channels have micro bore tubes of one or more diameters. The fluid-carrying channels have micro bore tubes of one or more lengths. The axle includes $2^N$ flow paths, where N is an integer greater than or equal to two. The set of radial holes corresponding to a first of the $2^N$ flow paths includes only one radial hole. The set of radial holes corresponding to a first of the $2^N$ flow paths includes a first radial hole to be aligned with a first of the input ports of the barrel and a second radial hole to be aligned with the output port of the barrel. The barrel includes position identifiers at a first end of the barrel. The flow rate of a fluid is selected by rotating the axle such that a reference point on a first end of the axle is aligned with a position identifier at the first end of the barrel. The apparatus further includes a key to engage a first end of the axle so as to aid a user in rotating the axle about the axis. The key includes one or more pins, each pin to be inserted into a respective slot at a first end of the axle, the key to aid a user in rotating the axle about the axis. The barrel includes notches at a first end of the barrel, and the key includes a stub to engage the notches at the first end of the barrel as the axle rotates about the axis, wherein the engagement of a notch by the stub provides a tactile feedback that is representative of a flow rate selection. The barrel includes notches at a first end of the barrel, and the axle includes a stub to engage the notches at the first end of the barrel as the axle rotates about the axis, wherein the engagement of a notch by the stub provides a tactile feedback that is representative of a flow rate selection. The axle includes a lock at a first end of the axle, and the key includes a peg to be inserted into the lock at the first end of the axle and snapped off within the lock such that rotation of the axle about the axis is prohibited. The key includes a tab lock that, in an activated state, restricts rotation of the axle about the axis. Each flow path is further defined by axial drain channels, and wherein a flow rate of fluid is selected by rotating the axle to a position so that a set of radial holes and axial drain channels are in alignment with one or more ports of the barrel. The interior cavity of the axle is in fluid communication with a destination of the fluid through a delivery line coupled to the output port of the barrel when a rotation of the axle results in an axial drain channel of the axle being in alignment with the output port of the barrel. The axle includes $2^N$ flow paths, where N is an integer greater than or equal to two, and wherein a first of the $2^N$ flow paths includes a first axial drain channel to be aligned with a first of the input ports of the barrel and a second axial drain channel to be aligned with the output port of the barrel.

In general, in one aspect, an apparatus for selecting a flow rate of a fluid includes a holding reservoir including an input reservoir port and output reservoir ports, the input reservoir port for introducing the fluid into the holding reservoir, each output reservoir port for dispensing fluid from the holding reservoir, an axle including an elongated cylindrical member having $2^N$ flow paths, where N is an integer greater than or equal to two, each flow path being defined by a corresponding set of radial holes, each set of radial holes comprising at least one radial hole that extends substantially between an outer surface of the axle and an interior cavity of the axle, a barrel including an elongated cylindrical member within which the axle is disposed, the barrel having input barrel ports and an output barrel port, the barrel being configured to enable the axle to rotate about an axis of rotation that extends along a length of the axle, N fluid-carrying channels, each fluid-carrying channel being coupled to a respective one of the output reservoir ports and a respective one of the input barrel ports, and a housing having a chamber within which the holding reservoir, the axle, the barrel, and the fluid-carrying channels are disposed, wherein a flow rate of a fluid is selected by rotating the axle to a position so that a set of radial holes is in alignment with one or more ports of the barrel and the holding reservoir is in fluid communication with the interior cavity of the axle via one or more fluid-carrying channels.

Implementations may include one or more of the following features. The holding reservoir is in fluid communication with a source of the fluid through a delivery line coupled to the input reservoir port. The interior cavity of the axle is in fluid communication with a destination of the fluid through a delivery line coupled to the output barrel port when a rotation of the axle results in a radial hole of the axle being in alignment with the output barrel port. The set of radial holes corresponding to a first of the $2^N$ flow paths includes only one radial hole. The set of radial holes corresponding to a first of the $2^N$ flow paths includes a first radial hole to be aligned with a first of the input barrel ports and a second radial hole to be aligned with the output barrel port. Each fluid-carrying channel includes a micro bore tube that controls a rate at which the fluid from the holding reservoir passes through the fluid-carrying channel. The apparatus further includes a key to engage a first end of the axle so as to aid a user in rotating the axle about the axis. The barrel and at least a portion of the housing form an integral unit. The holding reservoir and at least a portion of the housing form an integral unit.

DETAILED DESCRIPTION

Figure 1:
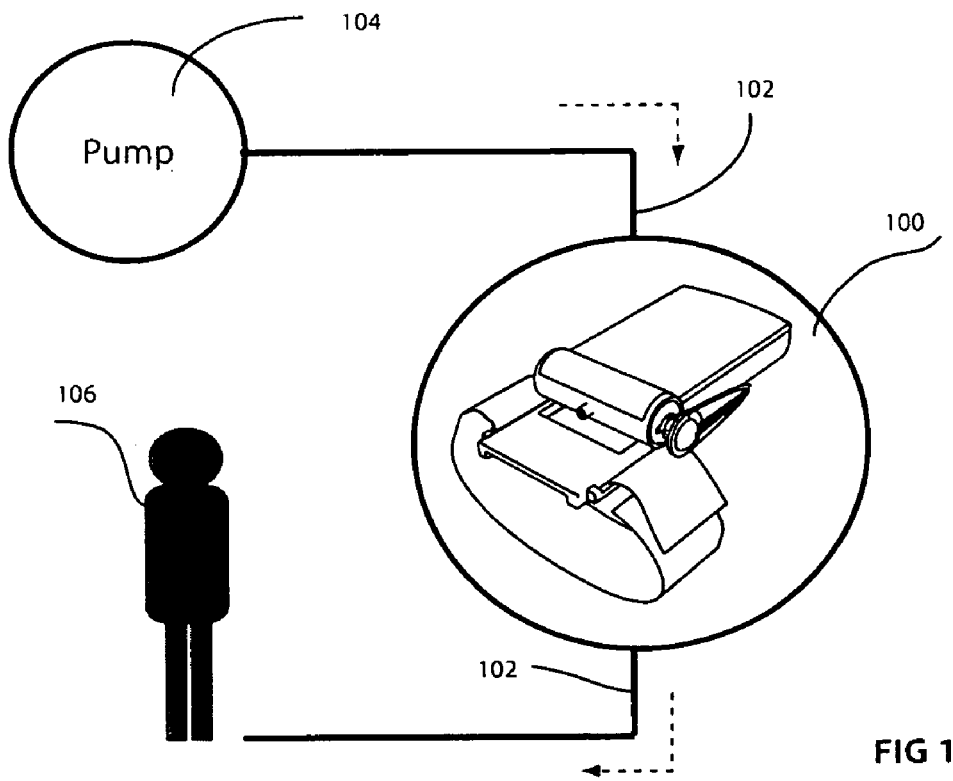
FIGS. 1-6 show flow controllers and associated components.

Referring to FIG. 1, a flow controller 100 regulates a flow of fluid 102 from a source, e.g., a fluid pump 104, to a final receiving point, e.g., a patient 106. In the context of a patient receiving medication, the flow controller 100 enables the patient 106 or a caregiver, e.g., a physician, to adjust a dose of medication to be administered to the patient 106 as is appropriate during the duration of the therapy. The flow controller 100 may be dimensioned so as to be worn by the patient 106, e.g., strapped onto the wrist (or arm) of the patient 106, thus allowing the flow controller 100 to be easily portable.

Figure 2A:
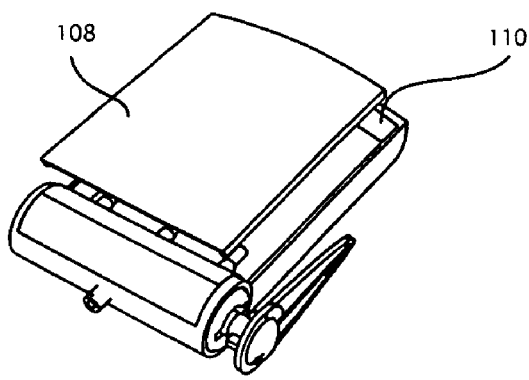
Figure 2B:
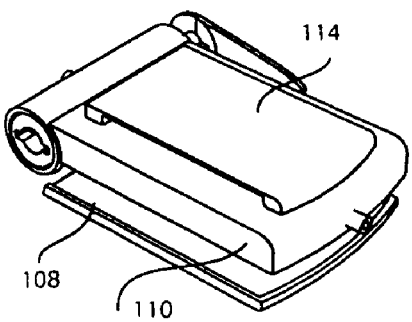
Figures 3A, 3B:
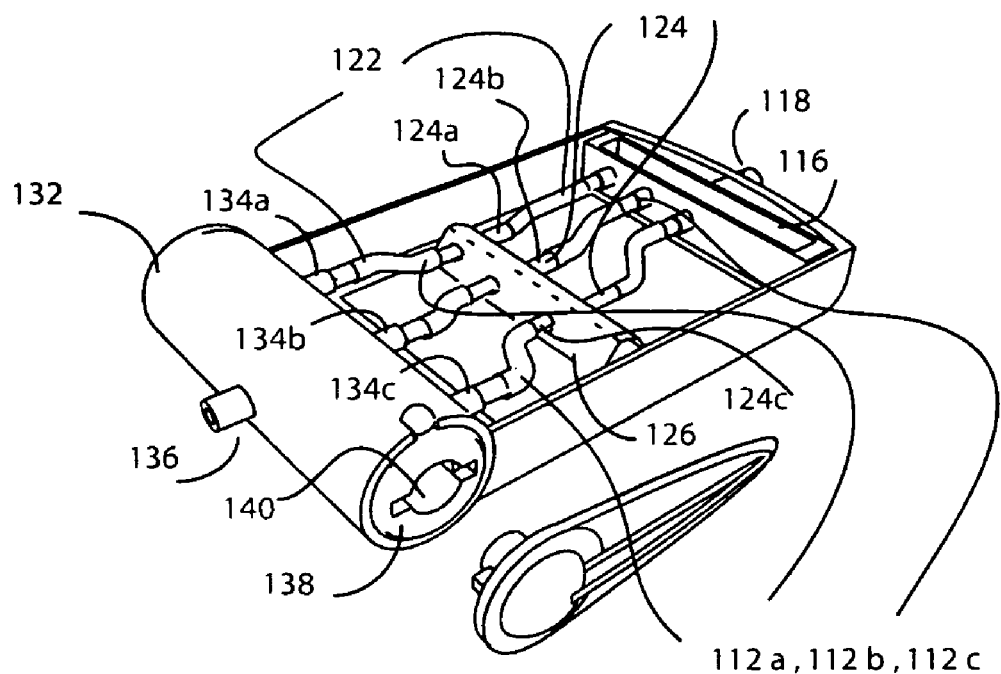
Figure 4:
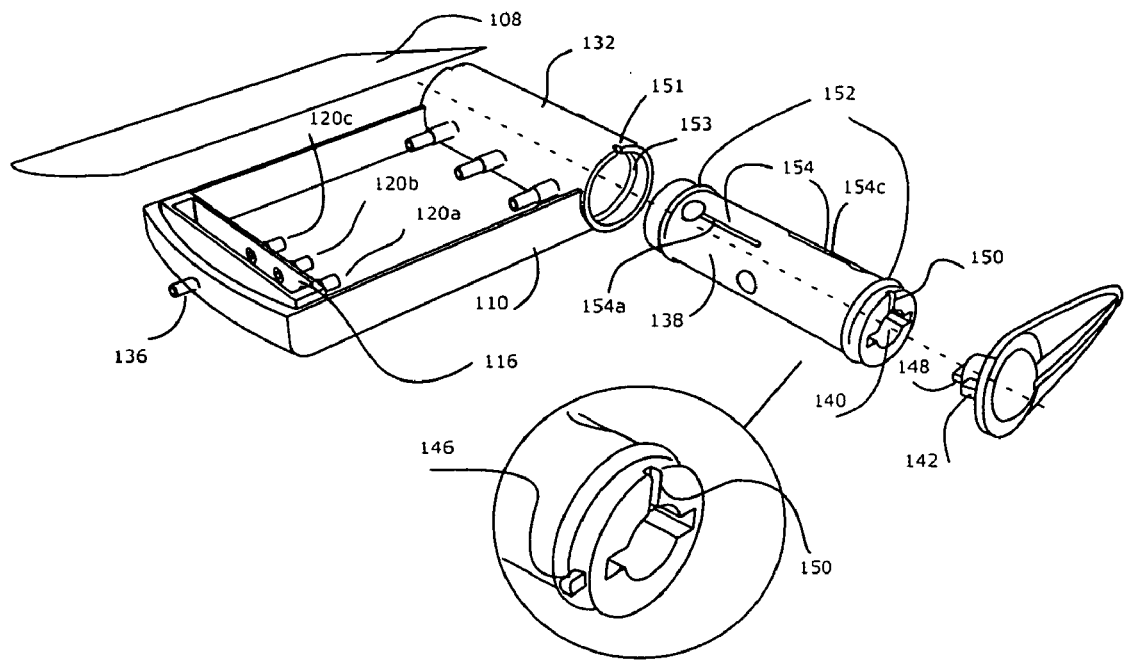

FIGS. 2-4 illustrate implementations of the flow controller 100. Referring to FIGS. 2A and 2B, the flow controller 100 includes a lid 108 and a base 110. The lid 108 and the base 110 can be manufactured (e.g., injection molded) using a polycarbonate resin or any other suitable material. Taken together, the lid 108 and the base 110 form a housing that encloses components of the flow controller 100. As shown in FIG. 2B, the base 110 includes a clip 114 that can be affixed to an arm or wrist band without requiring a docking module.

Referring also to FIGS. 3A and 3B, fluid 102 from the fluid pump 104 enters the flow controller 100 at a first end (e.g., the "pump end"), passes through one or more fluid-carrying channels 112a, 112b, 112c, and exits the flow controller at a second end (e.g., the "patient end"). A holding reservoir 116 disposed at the pump end of the flow controller 100 receives fluid 102 from the fluid pump 104 through a first delivery line that is coupled to an input port 118 of the holding reservoir 116. The holding reservoir 116 can be an injection molded container like compartment with minimal dead volume and a welded top lid. The holding reservoir 116 has three output ports 120a, 120b, 120c, each to receive a first end of a fluid-carrying channel 112a, 112b, 112c, respectively. Although the flow controller 100 is illustratively depicted with three fluid-carrying channels 112a, 112b, 112c, the flow controller 100 may be implemented with N number of fluid-carrying channels, where N is an integer greater than or equal to two.

In the example of FIG. 3A, each fluid-carrying channel 112a, 112b, 112c is formed using a combination of silicone tubes 122 and a glass micro bore tube 124. The silicone tubes 122 of the fluid-carrying channels 112a, 112b, 112c may be identical; the glass micro bore tubes 124 of the respective fluid-carrying channels 112a, 112b, 112c may be of different lengths, diameters, or combinations thereof. As shown in FIG. 3A, a structure 126 acts as a support element to hold the fluid-carrying channels 112a, 112b, 112c (more specifically, the glass micro bore tube 124) in place on the base 110 of the flow controller 100. A barrel 132 is disposed at the patient end of the flow controller 100. The barrel can be manufactured using a polycarbonate resin or any other suitable material. In the implementation of FIG. 3A, the barrel 132 is a generally elongated cylindrical hollow member that has three input ports 134a, 134b, 134c disposed on its outer surface. Each input port 134a, 134b, 134c is configured to receive a second end of a fluid-carrying carrying channel 112a, 112b, 112c, respectively. The barrel 132 also has an output port 136 to receive a second delivery line that is coupled to the final receiving point, e.g., a patient 106. A series of notches and/or position identifiers (e.g., position 1 through position 6 as described below in relation to FIG. 6) may be provided at one end of the barrel 132. Each notch or position identifier represents a flow rate selection as described below. Although the actual number of notches (or position identifiers) may vary from flow controller to flow controller, up to $2^N$ number of notches may be provided, where N is the number of fluid-carrying channels 112 provided within the flow controller 100.

An axle 138 may be manufactured using a high-density polyethylene material that is self-lubricating. Generally, the dimensions of the axle 138 and the barrel 132 are selected so that the axle 138 is free to rotate about an axis that extends along the length of the axle 138 (i.e., about the longitudinal axis of the axle 138) when the axle 138 is disposed within the barrel 132, while maintaining a close fit between an outer surface of the axle 138 and an inner surface of the barrel 132. In the implementation of FIG. 3A, the axle 138 is a generally elongated cylindrical member that includes a number of radial holes and axial drain channels. Each radial hole extends between the outer surface of the axle 138 and an interior cavity of the axle 138. When the axle 138 is rotated such that a set of radial holes of the axle 138 is aligned with one or more input ports 134a, 134b, 134c of the barrel 132, the interior cavity of the axle 138 and subsequently the output port 136, is in fluid communication with the holding reservoir 116 via one or more fluid-carrying channels 112a, 112b, 112c and the effective axial drain channels.

In the example of FIG. 3B, the fluid-carrying channels 112a, 112b, 112c (of FIG. 3A) are replaced with microbore tubings 160 made of polymer materials. As the inner lumen of polymer-based tubings are generally larger than glass tubes, the necessary lengths to achieve practical flow rates result in these tubes being coiled and taped with adhesive tapes 161.

Figure 5:
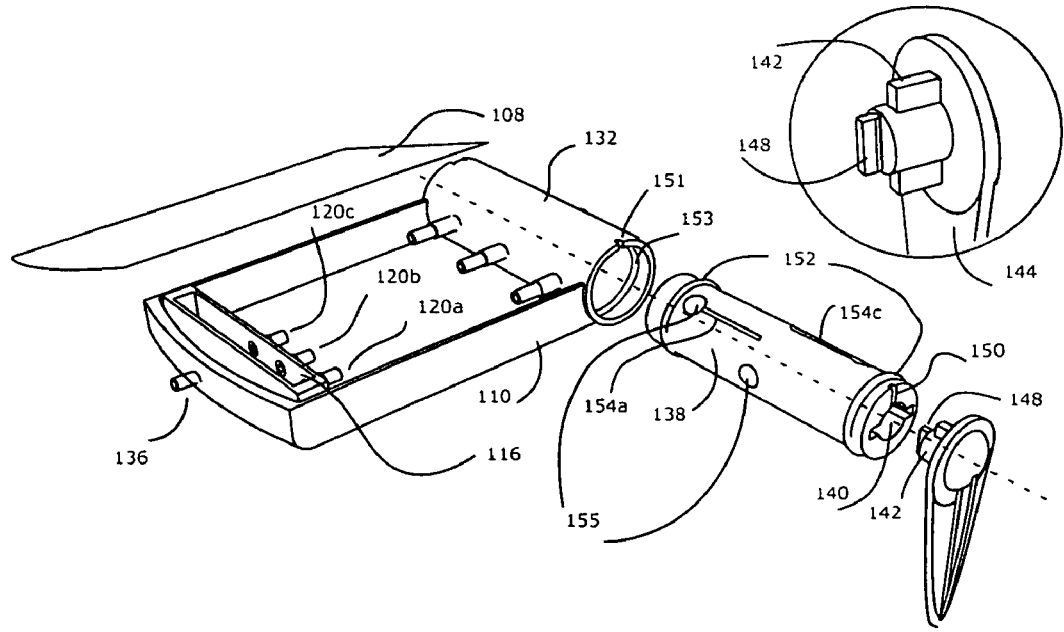

To aid the patient 106 or caregiver in rotating the axle 138 so that a set of radial holes of the axle 138 is perfectly aligned with one or more input ports 134a, 134b, 134c of the barrel 132 thereby selecting a desired flow rate, one end of the axle 138 may be manufactured with slots 140 to receive pins 142 of a key 144, an example of which is shown in FIG. 4. The axle 138 includes stubs 146 that glide over the inner surface of the barrel 132 upon which the notches are formed to provide tactile feedback representative of flow rate selections. In some implementations the stubs can be built onto the key 144 instead of the axle (not shown). In some implementations, once the axle 138 is rotated to a position (e.g., position 1 through position 6) indicative of the desired flow rate, a peg 148 of the key 144 may be inserted into a lock 150 of the axle 138 and snapped off to prevent further rotation of the axle 138, an example of which is shown in FIG. 5. In so doing, the peg 148 serves as a safety mechanism to prevent changes to the flow rate selection, e.g., by the patient 106. In some implementations, the key 144 includes a tab lock (not shown) that is engageable with the barrel to prevent rotation of the axle 138 while the tab lock is activated. Unlike the snapped off peg 148, the tab lock may be deactivated and reactivated to change the flow rate selection any of times during the course of therapy. The pins 148 of the key 144 are also engageable with the lid 108 for use in stowing the key 144 when the key 144 is not being used.

Figure 6:
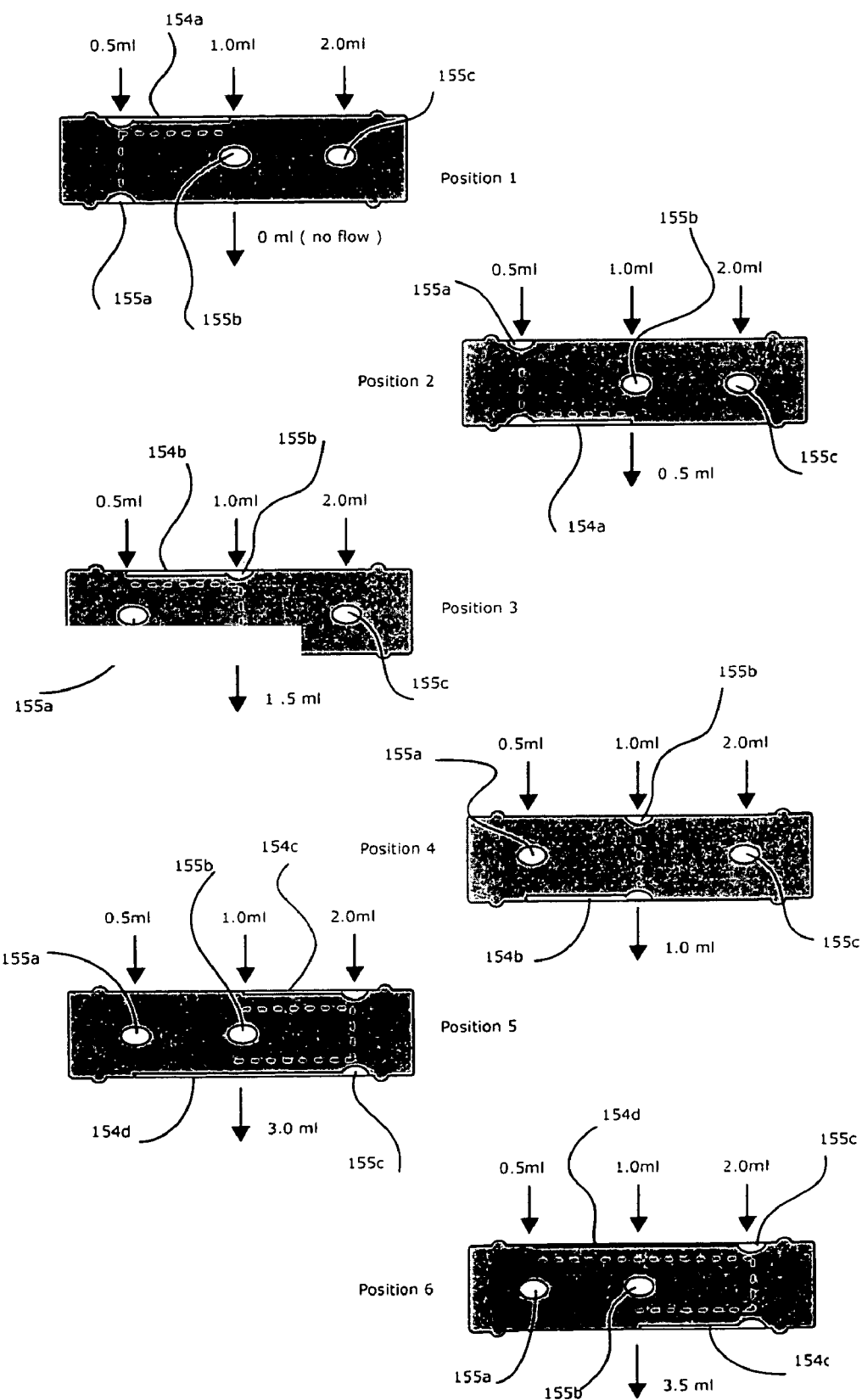

Suppose, for example, that the glass micro bore tubes 124 are selected so that the fluid-carrying channel 112a has a flow rate of 0.5 ml/hr, the fluid-carrying channel 112b has a flow rate of 1.0 ml/hr, and the fluid-carrying channel 112c has a flow rate of 2.0 ml/hr. In operation, e.g., as depicted in FIG. 6:

1. When the axle 138 is rotated to position 6, radial hole 155c of the axle 138 is aligned with the input port 134c of the barrel 132. The input ports 134a and 134b are in fluid communication with the radial hole 155c of the axle 138 via the axial drain channel 154d. The radial hole 155c of the axle 138 is in fluid communication with the output port 146 of the barrel 132 via the axial drain channel 154c. The interior cavity of the axle 138 is in fluid communication with the holding reservoir 116 via three fluid-carrying channels 112a, 112b, 112c resulting in a flow rate of 3.5 ml/hr being passed to the second delivery line.
2. When the axle 138 is rotated to position 5, radial hole 155c of the axle 138 is aligned with the input port 134c of the barrel 132. The input port 134b is in fluid communication with the radial hole 155c of the axle 138 via the axial drain channel 154c of the axle 138. The radial hole 155c of the axle is in fluid communication with the output port 146 of the barrel 132 via the axial drain channel 154d. The interior cavity of the axle 138 is in fluid communication with the holding reservoir 116 via two fluid-carrying channels 112b, 112c resulting in a flow rate of 3.0 ml/hr being passed to the second delivery line.
3. When the axle 138 is rotated to position 4, radial hole 155b of the axle 138 is aligned with the input port 134b of the barrel 132. In this position, the radial hole 155b of the axle 138 is also aligned with the output port 136 of the barrel 132. The interior cavity of the axle 138 is in fluid communication with the holding reservoir 116 via one fluid-carrying channels 112b resulting in a flow rate of 1.0 ml/hr being passed to the second delivery line.
4. When the axle 138 is rotated to position 3, radial hole 155b of the axle 138 is aligned with the input port 134b of the barrel 132. The input port 134a is in fluid communication with the radial hole 155b via the axial drain channel 154b of the axle 138. The interior cavity of the axle 138 is in fluid communication with the holding reservoir 116 via two fluid-carrying channels 112a and 112b resulting in a flow rate of 1.5 ml/hr being passed to the second delivery line.
5. When the axle 138 is rotated to position 2, radial hole 155a of the axle 138 is aligned with the input port 134a of the barrel 132. The radial hole 155a is in fluid communication with the output port 136 of the barrel 132 via the axial drain channel 154a. The interior cavity of the axle 138 is in fluid communication with the holding reservoir 116 via one fluid-carrying channel 112a resulting in a flow rate of 0.5 ml/hr being passed to the second delivery line.
6. When the axle 138 is rotated to position 1, radial hole 155a of the axle 138 is aligned with the input port 134a of the barrel 132. The radial hole 155a of the axle is in fluid communication with the input port 134b of the barrel 132 via the axial drain channel 154a but there is no fluid connection between the radial hole 155a and the output port 136 of the barrel 132. Accordingly, no fluid (i.e., a flow rate of 0 ml/hr) is passed to the second delivery line.

When the axle 138 is between discrete positions and none of the radial holes 134 are aligned with the input ports 134a, 134b, 134c and the output port 136, fluid 102 from the fluid-carrying channels 112 is effectively blocked from entering the axle 138 and fluid communication between the interior cavity of the axle 138 and the holding reservoir 116 cannot be achieved.

Referring again to FIGS. 4 and 5, the design of the axle can include end rings 152 matching grooves 153 on the inner side of the barrel. This ensures a tight seal and avoids leaks. The radius of curvature on the rings 152 will typically be smaller on the first ring that enters the barrel during assembly to ensure that the fit of the ring to the inner groove 153 is not compromised as a result of force applied to push the axle into the barrel.

In some implementations, the axle 138 and the barrel 132 are manufactured such that an insertion of the axle 138 into the barrel 132 results in the axle 138 being at position 1. Each 45° rotation of the axle 138 changes the flow rate selection by one position. For example, a 45° clockwise rotation of the axle 138 from position 1 to position 2 changes the flow rate from 0 to 0.5 ml/hr, a 45° counter-clockwise rotation of the axle 138 from position 1 to position 8 changes the flow rate from 0 to 3.5 ml/hr. In some implementations, the axle 138 and the barrel 132 are manufactured to restrict rotation of the axle 138 in one direction (e.g., clockwise-only or counter-clockwise only).

In some implementations, there are more than $2^N$ discrete positions between which the axle 138 may be rotated, with the corresponding number of flow paths and flow rates. With this arrangement, more incremental flow rates can be attained, e.g., 0.75 ml/hr, or 1.25 ml/hr flow rates for finer flow control of the 0.5 ml/hr and the 1.0 ml/hr fluid-carrying channels 112 of the example described above.

In some implementations, the barrel 132 and a portion of the housing (e.g., the lid 108 or the base 110) are manufactured as an integral unit. In some implementations, the holding reservoir 116 and a portion of the housing (e.g., the lid 108 or the base 110) are manufactured as an integral unit.

The ports of the holding reservoir 116 and the barrel 132 may be manufactured to have identical physical characteristics/dimensions so that fluid-carrying channels 112 of a particular type (e.g., silicone tubes having an internal diameter of ID mm) may be received by any of the ports without modification. By swapping out the micro bore tubes 124 of the fluid-carrying channels 112, any number of combinations of flow rates may be provided using the same flow controller.

In one example scenario, a hospital, clinic, or pharmacy (collectively referred to as "medication dispensing facility") stocks a single type of flow controller device that includes a lid, a base, a barrel, an axle, and a holding reservoir. The medication dispensing facility also stocks fluid-carrying channels formed by a single type of silicone tube (compatible with the ports of the device's barrel and holding reservoir) and micro bore tubes of various diameters and/or lengths. Each fluid-carrying channel is labeled with a flow rate that is based on its micro bore tube. For ease of assembly, a chart may be provided that depicts various combinations of fluid-carrying channels that may be assembled within the device to achieve desired flow rates. The chart may specify which ports of the holding reservoir and the barrel each fluid-carrying channel of a combination is to be coupled to in order to ensure that a subsequent rotation of the axle to a particular position results in a desired flow rate selection.

The flow controller 100 may be used with any portable, disposable mechanical/elastomeric infusion pump (defined by a fill capacity and flow rate) to provide selectable flow rates, thereby reducing or eliminating the need for medication dispensing facilities to stock a wide range of pumps.

Particular implementations of the subject matter described in this specification have been described. Other implementations are within the scope of the following claims. For example, the application of the flow controller is not necessarily limited to a medical treatment context. In some implementations, the holding reservoir includes multiple input ports, each to receive a fluid from a different fluid pump. Such an arrangement allows for increased flexibility in therapy, e.g., such as in situations where multi-drug therapy is desirable.

What is claimed is:

1. An apparatus for selecting a flow rate of a fluid, the apparatus comprising:
   an axle comprising an elongated cylindrical member having flow paths, each flow path being defined by a corresponding set of radial holes, each set of radial holes comprising at least one radial hole that extends substantially between an outer surface of the axle and an interior cavity of the axle, at least one of the flow paths being further defined by an axial drain channel that substantially extends longitudinally along a length of the axle; and
   a barrel comprising an elongated cylindrical member within which the axle is disposed, the barrel having input ports and an output port, the barrel being configured to enable the axle to rotate about an axis of rotation that extends along the length of the axle,
   wherein a flow rate of a fluid is selected by rotating the axle to a position so that a set of radial holes is in alignment with one or more ports of the barrel,
   wherein a length of the axial drain channel along a longitudinal axis of the axle is larger than a width of the axial drain channel along a radial axis of the axle.

2. The apparatus of claim 1, further comprising:
   a holding reservoir comprising an input port and output ports, the input port for introducing the fluid into the holding reservoir, each output port for dispensing fluid from the holding reservoir.

3. The apparatus of claim 2, wherein the holding reservoir is in fluid communication with a source of the fluid through a delivery line coupled to the input port of the holding reservoir.

4. The apparatus of claim 3, wherein the source of the fluid comprises a fluid pump.

5. The apparatus of claim 2, further comprising:
   fluid-carrying channels, each fluid-carrying channel being coupled to a respective one of the output port of the holding reservoir.

6. The apparatus of claim 1, wherein the interior cavity of the axle is in fluid communication with a destination of the fluid through a delivery line coupled to the output port of the barrel when a rotation of the axle results in a radial hole of the axle being in alignment with the output port of the barrel.

7. The apparatus of claim 6, wherein the destination of the fluid comprises a patient.

8. The apparatus of claim 1, further comprising:
   N fluid-carrying channels, where N is an integer greater than or equal to two, each fluid-carrying channel being coupled to a respective one of the input ports of the barrel.

9. The apparatus of claim 8, wherein each fluid-carrying channel comprises a micro bore tube that controls a rate at which fluid passes through the fluid-carrying channel.

10. The apparatus of claim 8, wherein the fluid-carrying channels have micro bore tubes of one or more diameters.

11. The apparatus of claim 8, wherein the fluid-carrying channels have micro bore tubes of one or more lengths.

12. The apparatus of claim 1, wherein the axle comprises $2^N$ flow paths, where N is an integer greater than or equal to two.

13. The apparatus of claim 12, wherein the set of radial holes corresponding to a first of the $2^N$ flow paths includes only one radial hole.

14. The apparatus of claim 12, wherein the set of radial holes corresponding to a first of the $2^N$ flow paths comprises a first radial hole to be aligned with a first of the input ports of the barrel and a second radial hole to be aligned with the output port of the barrel.

15. The apparatus of claim 1, wherein the barrel comprises position identifiers at a first end of the barrel.

16. The apparatus of claim 15, wherein the flow rate of a fluid is selected by rotating the axle such that a reference point on a first end of the axle is aligned with a position identifier at the first end of the barrel.

17. The apparatus of claim 1, further comprising:
   a key to engage a first end of the axle so as to aid a user in rotating the axle about the axis.

18. The apparatus of claim 17, wherein the key comprises one or more pins, each pin to be inserted into a respective slot at a first end of the axle, the key to aid a user in rotating the axle about the axis.

19. The apparatus of claim 17, wherein:
   the barrel comprises notches at a first end of the barrel; and
   the key comprises a stub to engage the notches at the first end of the barrel as the axle rotates about the axis, wherein the engagement of a notch by the stub provides a tactile feedback that is representative of a flow rate selection.

20. The apparatus of claim 17, wherein:
   the barrel comprises notches at a first end of the barrel; and
   the axle comprises a stub to engage the notches at the first end of the barrel as the axle rotates about the axis, wherein the engagement of a notch by the stub provides a tactile feedback that is representative of a flow rate selection.

21. The apparatus of claim 17, wherein:
   the axle comprises a lock at a first end of the axle; and
   the key comprises a peg to be inserted into the lock at the first end of the axle and snapped off within the lock such that rotation of the axle about the axis is prohibited.

22. The apparatus of claim 17, wherein the key comprises a tab lock that, in an activated state, restricts rotation of the axle about the axis.

23. The apparatus of claim 1, wherein each flow path is further defined by axial drain channels, and wherein a flow rate of fluid is selected by rotating the axle to a position so that a set of radial holes and axial drain channels are in alignment with one or more ports of the barrel.

24. The apparatus of claim 23, wherein the interior cavity of the axle is in fluid communication with a destination of the fluid through a delivery line coupled to the output port of the barrel when a rotation of the axle results in an axial drain channel of the axle being in alignment with the output port of the barrel.

25. The apparatus of claim 23, wherein the axle comprises $2^N$ flow paths, where N is an integer greater than or equal to two, and wherein a first of the $2^N$ flow paths comprises a first axial drain channel to be aligned with a first of the input ports of the barrel and a second axial drain channel to be aligned with the output port of the barrel.

26. An apparatus for selecting a flow rate of a fluid, the apparatus comprising:
  a holding reservoir comprising an input reservoir port and output reservoir ports, the input reservoir port for introducing the fluid into the holding reservoir, each output reservoir port for dispensing fluid from the holding reservoir;
  an axle comprising an elongated cylindrical member having $2^N$ flow paths, where N is an integer greater than or equal to two, each flow path being defined by a corresponding set of radial holes, each set of radial holes comprising at least one radial hole that extends substantially between an outer surface of the axle and an interior cavity of the axle, at least one of the flow paths being further defined by an axial drain channel that substantially extends longitudinally along a length of the axle;
  a barrel comprising an elongated cylindrical member within which the axle is disposed, the barrel having input barrel ports and an output barrel port, the barrel being configured to enable the axle to rotate about an axis of rotation that extends along the length of the axle;
  N fluid-carrying channels, each fluid-carrying channel being coupled to a respective one of the output reservoir ports and a respective one of the input barrel ports; and
  a housing having a chamber within which the holding reservoir, the axle, the barrel, and the fluid-carrying channels are disposed;
  wherein a flow rate of a fluid is selected by rotating the axle to a position so that a set of radial holes is in alignment with one or more ports of the barrel and the holding reservoir is in fluid communication with the interior cavity of the axle via one or more fluid-carrying channels,
  wherein a length of the axial drain channel along a longitudinal axis of the axle is larger than a width of the axial drain channel along a radial axis of the axle.

27. The apparatus of claim 26, wherein the holding reservoir is in fluid communication with a source of the fluid through a delivery line coupled to the input reservoir port.

28. The apparatus of claim 26, wherein the interior cavity of the axle is in fluid communication with a destination of the fluid through a delivery line coupled to the output barrel port when a rotation of the axle results in a radial hole of the axle being in alignment with the output barrel port.

29. The apparatus of claim 26, wherein the set of radial holes corresponding to a first of the $2^N$ flow paths includes only one radial hole.

30. The apparatus of claim 26, wherein the set of radial holes corresponding to a first of the $2^N$ flow paths comprises a first radial hole to be aligned with a first of the input barrel ports and a second radial hole to be aligned with the output barrel port.

31. The apparatus of claim 26, wherein each fluid-carrying channel comprises a micro bore tube that controls a rate at which the fluid from the holding reservoir passes through the fluid-carrying channel.

32. The apparatus of claim 26, further comprising:
  a key to engage a first end of the axle so as to aid a user in rotating the axle about the axis.

33. The apparatus of claim 26, wherein the barrel and at least a portion of the housing form an integral unit.

34. The apparatus of claim 26, wherein the holding reservoir and at least a portion of the housing form an integral unit.

* * * * *